(12) United States Patent
Salvati et al.

(10) Patent No.: US 10,488,407 B2
(45) Date of Patent: Nov. 26, 2019

(54) MASS DETECTION THROUGH REDOX COUPLING

(71) Applicant: QORVO US, INC., Greensboro, NC (US)

(72) Inventors: Michael Salvati, Minnetrista, MN (US); Ian Robert Harmon, Minneapolis, MN (US)

(73) Assignee: QORVO US, INC., Greensboro, NC (US)

( * ) Notice: Subject to any disclaimer, the term of this patent is extended or adjusted under 35 U.S.C. 154(b) by 332 days.

(21) Appl. No.: 15/511,130

(22) PCT Filed: Sep. 14, 2015

(86) PCT No.: PCT/US2015/049912
§ 371 (c)(1),
(2) Date: Mar. 14, 2017

(87) PCT Pub. No.: WO2016/044132
PCT Pub. Date: Mar. 24, 2016

(65) Prior Publication Data
US 2017/0276670 A1    Sep. 28, 2017

Related U.S. Application Data

(60) Provisional application No. 62/050,585, filed on Sep. 15, 2014.

(51) Int. Cl.
*G01N 33/53*       (2006.01)
*C12Q 1/26*        (2006.01)
(Continued)

(52) U.S. Cl.
CPC .............. *G01N 33/53* (2013.01); *C12Q 1/26* (2013.01); *G01N 29/022* (2013.01);
(Continued)

(58) Field of Classification Search
CPC .............. C12Q 1/26; G01N 2291/012; G01N 2291/0255; G01N 2291/0256;
(Continued)

(56) References Cited

U.S. PATENT DOCUMENTS 4,999,284 A    3/1991  Ward et al.
5,104,944 A *  4/1992  Goldberg ............... C08G 73/10
                                              525/436

(Continued)

FOREIGN PATENT DOCUMENTS

JP    1990-200200 A    8/1990
JP    1991-503567 A    8/1991
(Continued)

OTHER PUBLICATIONS

Ying-Chung Chen, Wei-Tsai Chang, Kuo-Sheng Kao, Chun-Hung Yang, & Chein-Chuan Cheng, e Liquid Sensor Using in Film Bulk Acoustic Resonator with C-Axis Tilted AlN Films, 2013/245095, Journal of Nanomaterials vol. 2013, Article ID 245095, 8 pages (Year: 2013).*

(Continued)

*Primary Examiner* — Francis C Gray
(74) *Attorney, Agent, or Firm* — Mueting, Raasch & Gebhardt, P.A.

(57) ABSTRACT

Redox of an analyte is coupled with redox of a precipitation precursor to generate a precipitating molecule that precipitates on the surface of a thin film bulk acoustic resonance (TFBAR) to allow mass detection of the precipitation molecule as a surrogate for the analyte. This disclosure describes, among other things, detection of an analyte using a TFBAR operating at a high frequency without direct binding of the analyte on a surface of the TBAR. Detection of the analyte is indirect with a precipitating molecule serving as a surrogate for the analyte.

20 Claims, 6 Drawing Sheets

(51) Int. Cl.
*G01N 33/543* (2006.01)
*G01N 29/02* (2006.01)
*G01N 29/036* (2006.01)
*G01N 29/34* (2006.01)

(52) U.S. Cl.
CPC ......... *G01N 29/036* (2013.01); *G01N 29/348* (2013.01); *G01N 33/54373* (2013.01); *G01N 2291/012* (2013.01); *G01N 2291/0255* (2013.01); *G01N 2291/0256* (2013.01); *G01N 2291/0426* (2013.01)

(58) Field of Classification Search
CPC ......... G01N 2291/0426; G01N 29/022; G01N 29/036; G01N 29/348; G01N 33/53; G01N 33/54373
See application file for complete search history.

(56) References Cited

U.S. PATENT DOCUMENTS

| | | | |
|---|---|---|---|
| 5,217,594 A * | 6/1993 | Henkens | C12Q 1/003 |
| | | | 204/403.04 |
| 5,707,820 A * | 1/1998 | Wilsey | C12Q 1/26 |
| | | | 435/14 |
| 5,932,953 A | 8/1999 | Drees et al. | |
| 5,936,150 A * | 8/1999 | Kobrin | G01N 5/02 |
| | | | 310/324 |
| 6,060,818 A * | 5/2000 | Ruby | H03H 3/02 |
| | | | 29/25.35 |
| 6,316,861 B1 | 11/2001 | Ballandras et al. | |
| 6,350,368 B1 * | 2/2002 | Willner | C12Q 1/004 |
| | | | 205/777.5 |
| 6,355,498 B1 * | 3/2002 | Chan | B81C 1/00142 |
| | | | 438/48 |
| 6,603,371 B2 | 8/2003 | Nakao et al. | |
| 6,842,088 B2 * | 1/2005 | Yamada | B06B 1/0644 |
| | | | 310/322 |
| 7,135,295 B1 | 11/2006 | Willner et al. | |
| 7,964,144 B1 * | 6/2011 | Nordin | G01N 33/5005 |
| | | | 422/50 |
| 8,252,606 B2 | 8/2012 | Hulko et al. | |
| 8,409,875 B2 | 4/2013 | Johal et al. | |
| 9,835,595 B2 * | 12/2017 | Webster | G01N 29/022 |
| 2002/0067106 A1 * | 6/2002 | Sunwoo | H03H 3/02 |
| | | | 310/330 |
| 2003/0049511 A1 * | 3/2003 | Ritts | C08J 5/2256 |
| | | | 429/431 |
| 2004/0150296 A1 * | 8/2004 | Park | G01N 29/022 |
| | | | 310/324 |
| 2005/0148065 A1 | 7/2005 | Zhang et al. | |
| 2006/0133953 A1 * | 6/2006 | Zhang | B82Y 15/00 |
| | | | 422/400 |
| 2006/0232281 A1 | 10/2006 | Vittorio et al. | |
| 2007/0202559 A1 * | 8/2007 | Hasenbank | C12Q 1/26 |
| | | | 435/11 |
| 2009/0059230 A1 | 3/2009 | Hermens | |
| 2009/0130698 A1 | 5/2009 | Worden et al. | |
| 2009/0282902 A1 | 11/2009 | Warthoe | |
| 2010/0105079 A1 | 4/2010 | Warthoe | |
| 2016/0291005 A1 * | 10/2016 | Salvati | G01N 33/54373 |

FOREIGN PATENT DOCUMENTS

| | | |
|---|---|---|
| JP | 2000-151352 A | 5/2000 |
| JP | 2002-171153 A | 6/2002 |
| JP | 2006-520899 A | 9/2006 |
| JP | 2010-529422 A | 8/2010 |
| JP | 2007-121188 A | 5/2017 |
| WO | WO 89/09937 A1 | 10/1989 |
| WO | WO 2016/044132 A1 | 3/2016 |

OTHER PUBLICATIONS

U.S. Appl. No. 62/050,585, filed Sep. 15, 2014, Salvati et al.
PCT/US2015/049912, Sep. 14, 2015, Salvati et al.
International Patent Application No. PCT/US2015/049912, filed Sep. 14, 2015; International Preliminary Report on Patentability dated Mar. 21, 2017, 6 pages.
International Patent Application No. PCT/US2015/049912, filed Sep. 14, 2015; International Search Report / Written Opinion dated Dec. 8, 2015, 9 pages.
European Patent Application No. 15842341.8, filed Sep. 14, 2015 (International filing date); Extended European Search Report dated Jan. 29, 2018, 9 pages.
Chen, et al., "Highly sensitive detection of organophosphorus pesticides by acetylcholinesterase-coated thin film bulk acoustic resonator mass-loading sensor", 2013, *Biosensors and Bioelectrics* 41:163-167. Available online Aug. 30, 2012.
Japanese Patent Application No. 2017-533725, filed Mar. 14, 2017; Office Action dated Mar. 27, 2019, English language translation included, 6 pgs.

* cited by examiner

FIG. 8

MASS DETECTION THROUGH REDOX COUPLING

RELATED APPLICATIONS

This application is the § 371 U.S. National Stage of International Application No. PCT/US2015/049912, filed 14 Sep. 2015, which claims the benefit of U.S. Provisional Patent Application No. 62/050,585, filed on Sep. 15, 2014, the disclosures of which are hereby incorporated herein by reference in their entireties to the extent that they do not conflict with the disclosure presented herein.

FIELD

This disclosure generally relates to, among other things, analyte detection using thin film bulk acoustic resonators (TFBARs).

BACKGROUND

Piezoelectric devices such as thin film bulk acoustic resonators (TFBARs) and technologies like quartz crystal microbalances (QCM) have been employed as mass detectors for some time. One application of piezoelectric resonators is in detecting very small quantities of materials. Piezoelectric resonators used as sensors in such applications are sometimes called "micro-balances." A piezoelectric resonator is typically constructed as a thin, planar layer of crystalline or polycrystalline piezoelectric material sandwiched between two electrode layers. When used as a sensor, the resonator is exposed to the material being detected to allow the material to bind on a surface of the resonator.

One conventional way of detecting the amount of the material bound on the surface of a sensing resonator is to operate the resonator as an oscillator at its resonant frequency. As the material being detected binds on the resonator surface, the oscillation frequency of the resonator is reduced. The change in the oscillation frequency of the resonator, presumably caused by the binding of the material on the resonator surface, is measured and used to calculate the amount of the material bound on the resonator or the rate at which the material accumulates on the resonator surface. A change in phase may also be used to determine the amount or rate of material bound or binding to the resonator surface.

The use of piezoelectric resonator sensors in immunoassays has been described. In such immunoassays, mass change attributable to immunological reaction between an antigen and an antibody, one of which is bound to the surface of the resonator prior to the assay, is determined.

However, in some circumstances it may be desirable to detect the presence of an analyte in a sample without binding the analyte to the surface of a resonator; e.g., via an antibody bound to the surface of the resonator.

SUMMARY

This disclosure describes, among other things, detection of an analyte using a TFBAR operating at a high frequency without direct binding of the analyte on a surface of the TBAR. Detection of the analyte is indirect with a precipitating molecule serving as a surrogate for the analyte. The analyte is capable of being oxidized or reduced and donating or withdrawing electrons to or from a soluble precipitation precursor or to or from an intermediate electron transfer agent that can donate or withdraw electrons to or from the soluble precipitation precursor or another intermediate electron transfer agent. Oxidization or reduction of the precursor results in the precipitating molecule.

Accordingly, the precipitating molecule is a redox reaction product, where the reaction product is oxidized or reduced from a soluble precursor to an insoluble or precipitating reaction product. Precipitation of the redox reaction product on the surface of the TFBAR alters the mass on the surface thereby changing a resonance characteristic of the TFBAR. The kinetics of the change or the magnitude of the change can be correlated with the amount of analyte in the sample.

This disclosure also describes, among other things, detection of activity of a redox enzyme using a TFBAR. The TFBAR may be operated at a high frequency. Detection of redox enzyme activity can be accomplished in a manner similar to detection of an analyte described above. A test sample putatively including a redox enzyme can be combined with a substrate that can be oxidized or reduced by the enzyme. The oxidization or reduction of the substrate can be coupled to oxidization or reduction of a soluble precursor via a redox cascade that results in a molecule precipitating on a surface of the TFBAR. The change in mass on the surface of the TFBAR can be correlated with activity of the enzyme in the test sample.

One or more embodiments of the apparatuses, systems or methods described herein provide one or more advantages over prior sensors, devices, systems or methods for detecting an analyte. Embodiments of the methods, sensors, devices, and systems disclosed herein allow for detection of molecules that may not be particularly amenable to measurement by immunoassay or binding event. Embodiments of the methods, sensors, devices, and systems disclosed herein create a universal sensor that can be utilized with a variety of specific redox enzymes. These and other advantages will be readily understood by those of skill in the art from the following detailed description.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description several specific embodiments of compounds, compositions, sensors, devices, systems and methods are disclosed. It is to be understood that other embodiments are contemplated and may be made without departing from the scope or spirit of the present disclosure. The following detailed description, therefore, is not to be taken in a limiting sense.

This disclosure describes, among other things, detection of an analyte using a TFBAR operating at a high frequency without direct binding of the analyte on a surface of the TFBAR. Detection of the analyte is indirect with a precipitating molecule serving as a surrogate for the analyte. The analyte is capable of being oxidized or reduced and donating or withdrawing electrons to or from a soluble precipitation precursor or to or from an intermediate electron transfer agent that can donate or withdraw electrons to or from the soluble precipitation precursor or another intermediate electron transfer agent. Oxidization or reduction of the precursor, depending on the precursor, results in the precipitating molecule.

One or more intermediate electron transfer agent or redox reagent can be attached to the surface of the TFBAR. The immobilized intermediate electron transfer agent can oxidize or reduce one or more of the soluble precipitation precursor, the target analyte, a cofactor, or any other redox molecule employed in a detection assay. In some embodiments, no intermediate electron transfer agent or other assay reagent is coupled to the surface of the TFBAR, as precipitation of the precipitating molecule on the surface of the TFBAR can still occur. However, it is preferable that at least one intermediate electron transfer agent or other redox reagent is immobilized on the surface of the TFBAR so that at least a portion of the cascade of redox reactions takes place in proximity to the surface of the TFBAR to increase the likelihood that the precipitating molecule will be formed in proximity to the surface of the TFBAR. In addition, immobilizing a redox reagent on the surface of a test resonator but not a reference resonator allows the reagent to be omitted from the solution or suspension introduced over the test and reference resonators and thus can reduce or eliminate the amount of precipitation on the reference sensor due to the absence of the redox reagent.

The analyte and the soluble precipitation precursor can be mixed prior to moving across the resonator or as they are being moved across the sensor. Preferably, redox of the analyte is not capable of being coupled to redox of the soluble precipitation precursor before the assay mixture is in contact with the TFBAR. Accordingly, at least one redox reagent required for coupling redox of the analyte to redox of the soluble precipitation precursor is not present in the assay mixture until the mixture is contacted with the TFBAR. This can be accomplished by immobilizing a redox reagent, such as an intermediate electron transfer agent, to the surface of the TFBAR, by mixing the analyte sample with the other reagents at the time of introduction across the TFBAR, or the like.

In preferred embodiments, the redox state of each of the reagents used is selected based on the expected redox state of the analyte to avoid initiation of a redox cascade and generation of the precipitating molecule prior to contact of the assay mixture with the TFBAR and to avoid false positive results or overestimations of the amount of analyte present.

Sensors, Devices and Systems

The sensors disclosed herein include at least one thin film resonator sensor, such as a thin film bulk acoustic resonator (TFBAR) sensor. A TFBAR sensor includes a piezoelectric layer, or piezoelectric substrate, and input and output transducer. TFBAR sensors are small sensors making the technology suitable for use in handheld devices. Accordingly, a handheld device for detecting target analytes comprising a sensor described herein is contemplated.

Figure 1A:
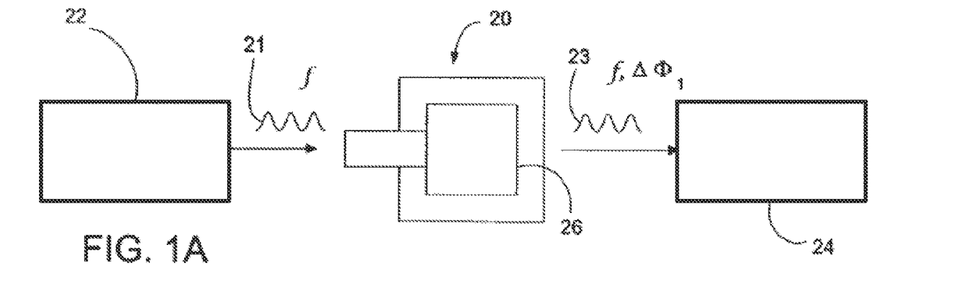
FIGS. 1A-1C are schematic diagrams illustrating the operational principles of some embodiments of thin film bulk acoustic resonator (TFBAR) sensing devices.
Figure 1B:
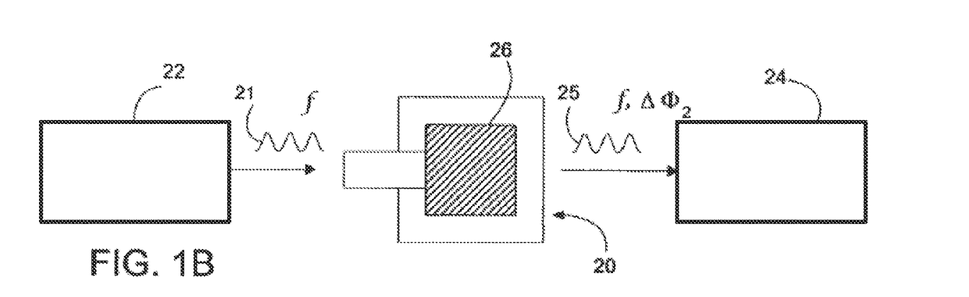

Turning now to the drawings with reference to FIGS. 1A and 1B, general operating principles of embodiments of a bulk-acoustic wave piezoelectric resonator 20 used as a sensor to detect an analyte are shown. The resonator 20 typically includes a planar layer of piezoelectric material bounded on opposite sides by two respective metal layers which form the electrodes of the resonator. The two surfaces of the resonator are free to undergo vibrational movement when the resonator is driven by a signal within the resonance band of the resonator. When the resonator is used as a sensor, at least one of its surfaces is adapted to include at least one intermediate electron transfer agent for use in coupling a redox reaction of an analyte with a redox reaction for converting a soluble precipitation precursor to a precipitating molecule. Precipitation of the precipitating molecule on the surface of the resonator alters the resonant characteristics of the resonator, and the changes in the resonant characteristics are detected and interpreted to provide quantitative information regarding the material (analyte) being detected.

By way of example, such quantitative information can be obtained by detecting a change in the insertion or reflection coefficient phase shift of the resonator caused by the precipitation of the precipitating molecule on the surface of the resonator. Such sensors differ from those that operate the resonator as an oscillator and monitor changes in the oscillation frequency. Rather such sensors insert the resonator in the path of a signal of a pre-selected frequency and monitor the variation of the insertion or reflection coefficient phase shift caused by the binding of the material being detected on the resonator surface. Of course, sensors that monitor changes in oscillation frequency may also be employed.

In more detail, FIG. 1A shows the resonator 20 before the precipitating molecule has precipitated on its surface 26. The depicted resonator 20 is electrically coupled to a signal source 22, which provides an input electrical signal 21 having a frequency f within the resonance band of the resonator. The input electrical signal is coupled to the resonator 20 and transmitted through the resonator to provide an output electrical signal 23. In the depicted embodiment, the output electrical signal 23 is at the same frequency as the input signal 21, but differs in phase from the input signal by a phase shift $\Delta\Phi_1$, which depends on the piezoelectric properties and physical dimensions of the resonator. The output signal 23 is coupled to a phase detector 24 which provides a phase signal related to the insertion phase shift.

FIG. 1B shows the sensing resonator 20 with the precipitating molecule being precipitated on its surface 26. The same input signal is coupled to the resonator 20. Because the resonant characteristics of the resonator are altered by the binding of the material as a perturbation, the insertion phase shift of the output signal 25 is changed to $\Delta\Phi_2$. The change in insertion phase shift caused by the binding of the material is detected by the phase detector 24. The measured phase shift change is related to the amount of the material bound on the surface of the resonator.

Figure 1C:
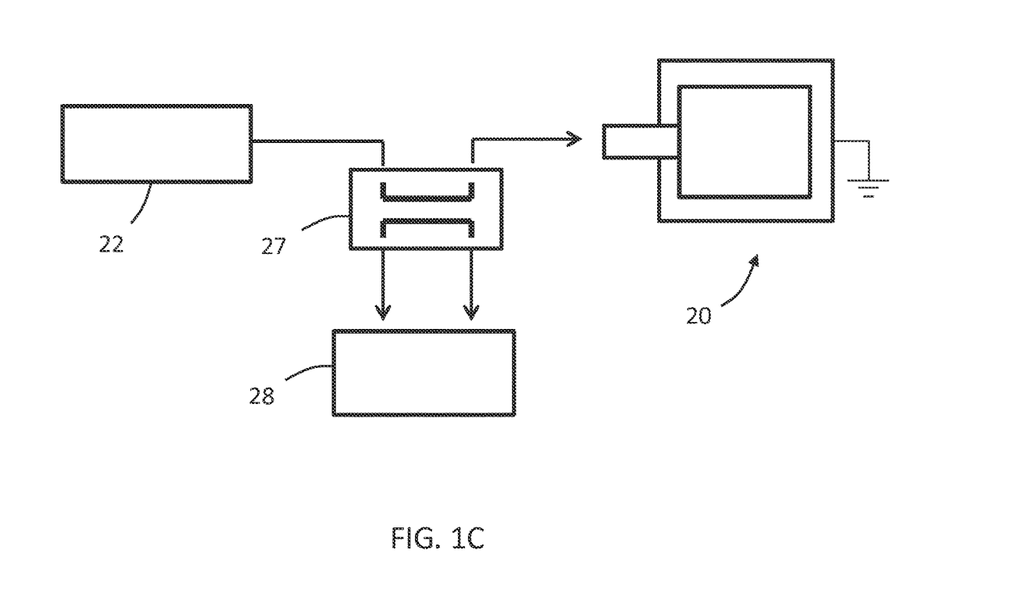

FIG. 1C shows an alternative to measuring the insertion phase of the resonator. A directional coupler 27 is added between the signal source 22 and the resonator 20 with the opposite electrode grounded. A phase detector 28 is configured to measure the phase shift of the reflection coefficient as a result of material binding to the resonator surface. Of course, reflection phase shift or any other suitable change in resonance characteristic of the sensor may be employed.

Other TFBAR phase-shift sensors that may be employed with the signal amplification aspects described herein include those described in, for example, U.S. Pat. No. 8,409,875 entitled "RESONATOR OPERATING FREQUENCY OPTIMIZATION FOR PHASE-SHIFT DETECTION SENSORS," which patent is hereby incorporated herein by reference in its entirety to the extent that it does not conflict with the disclosure presented herein. For example, sensor apparatuses may include (i) a sensing resonator comprising one or more bound electron transfer agent; (ii) actuation circuitry configured to drive the sensing resonator in an oscillating motion; (iii) measurement circuitry arranged to be coupled to the sensing resonator and configured to measure one or more resonator output signals representing resonance characteristics of the oscillating motion of the sensing resonator; and (iv) a controller operatively coupled with the actuation and measurement circuitry. The controller can be interfaced with data storage containing instructions that, when executed, cause the controller to adjust the frequency at which the actuation circuitry drives the sensing resonator to maintain a resonance point of the sensing resonator. Accordingly, sensing may be accomplished by actuating the TFBAR into an oscillating motion; measuring one or more resonator output signals representing resonance characteristics of the oscillating motion of the TFBAR; and adjusting the actuation frequency of the sensing resonator to maintain a resonance point of the TFBAR. In embodiments, the frequency at which the actuation circuitry drives the sensing resonator is a frequency of maximum group delay.

Such phase detection approaches can be advantageously used with piezoelectric resonators of different resonant frequencies.

In various embodiments, TFBARs for use with the methods, devices, and system described herein have resonance frequencies of about 500 MHz or greater, such as about 700 MHz or greater, about 900 MHz or greater, about 1 MHz or greater, about 1.2 MHz or greater, about 1.5 GHz or greater, about 1.8 GH or greater, about 2 GHz or greater, 2.2 GHz or greater, 2.5 GHz or greater, about 3 GHZ or greater, or about 5 GHZ or greater can provide enhanced sensitivity when used with amplification element mediated mass loaded, which is described in more detail below. In embodiments, the TFBARs have resonance frequencies of from about 500 MHz to about 5 GHz, such as from about 900 MHz to about 3 GHz, or from about 1.2 GHz to about 2.5 GHz. Some of such frequencies are substantially higher than frequencies of previously described piezoelectric resonators.

The sensing resonators described herein are thin-film resonators. Thin film resonators comprise a thin layer of piezoelectric material deposited on a substrate, rather than using, for example, AT-cut quartz. The piezoelectric films typically have a thickness of less than about 5 micrometers, such as less than about 2 micrometers, and may have thicknesses of less than about 100 nanometers. Thin-film resonators are generally preferred because of their high resonance frequencies and the theoretically higher sensitivities. Depending on the applications, a thin-film resonator used as the sensing element may be formed to support either longitudinal or shear bulk-acoustic wave resonant modes. Preferably, the sensing element is formed to support shear bulk-acoustic wave resonant modes, as they are more suitable for use in a liquid sample.

Additional details regarding sensor devices and systems that may employ thin film resonators (TFRs) are described in, for example, U.S. Pat. No. 5,932,953 issued Aug. 3, 1999 to Drees et al., which patent is hereby incorporated herein by reference in its entirety to the extent that it does not conflict with the disclosure presented herein.

TFR sensors may be made in any suitable manner and of any suitable material. By way of example, a resonator may include a substrate such as a silicon wafer or sapphire, a Bragg mirror layer or other suitable acoustic isolation means, a bottom electrode, a piezoelectric material, and a top electrode.

Any suitable piezoelectric material may be used in a TFR. Examples of suitable piezoelectric substrates include lithium tantalate ($LiTaO_3$), lithium niobate ($LiNbO_3$), Zinc Oxide (ZnO), aluminum nitride (AlN), plumbum zirconate titanate (PZT) and the like.

Electrodes may be formed of any suitable material, such as aluminum, tungsten, gold, titanium, molybdenum, or the like. Electrodes may be deposited by vapor deposition or may be formed by any other suitable process.

Any suitable device or system may employ a thin film resonator and amplification as described herein. By way of example and with reference to FIG. 2, a system for detecting an analyte may include a container 10 (or more than one container), the thin film resonator 20, actuation circuitry 22, measurement circuitry 29, and control electronics 30. A fluid path couples the one or more containers 10 to the resonator 20. The control electronics 30 are operably coupled to the actuation circuitry and the measurement circuitry. In embodiments, control electronics 30 are configured to modify the frequency at which the actuation circuitry 22 oscillates the resonator 20 based on input from the measurement circuitry 29.

Figure 2:
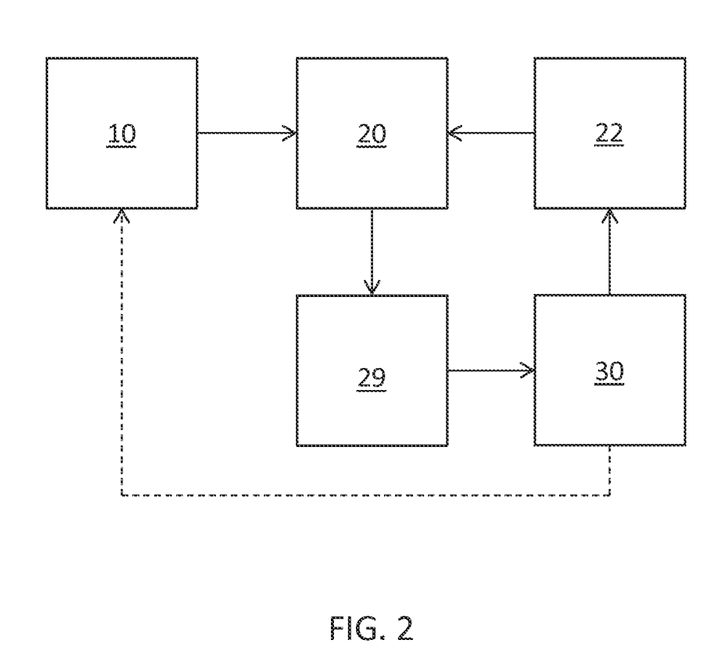
FIG. 2 is a schematic diagram showing components of an embodiment of a TFBAR system for detecting an analyte.

Still with reference to FIG. 2, the container 10 (or more than one container) may house an intermediate electron transfer agent, soluble precipitation precursor, and optionally an analyte molecule. Each of these reagents is described in more detail below. Control electronics 30 may control the flow of such reagents from container 10 to resonator 20; e.g. via a pump, vacuum, or the like.

Any suitable control electronics 30 may be employed. For example, control electronics may include a processor, controller, memory, or the like. Memory may include computer-readable instructions that, when executed by processor or controller cause the device and control electronics to perform various functions attributed to device and control electronics described herein. Memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Control electronics 30 may include any one or more of a microprocessor, a controller, a digital signal processor (DSP), an application specific integrated circuit (ASIC), a field-programmable gate array (FPGA), or equivalent discrete or integrated logic circuitry. In some examples, control electronics 30 may include multiple components, such as any combination of one or more microprocessors, one or more controllers, one or more DSPs, one or more ASICs, or one or more FPGAs, as well as other discrete or integrated logic circuitry. The functions attributed to control electronics herein may be embodied as software, firmware, hardware or any combination thereof.

Analyte-Coupled Redox Cascade

In the methods, devices and systems described herein, molecular recognition of a sample comprising an analyte capable of undergoing a redox reaction can allow for detection of the analyte in a sample. The redox of the analyte is coupled to redox of a soluble precipitation precursor through one or more intermediate electron transfer agents and cofactors, if needed or desired. The redox cascade results in conversion of the soluble precipitation precursor to a precipitating molecule, which can precipitate on the surface of a TFBAR. TFBAR sensors, at higher frequency ranges described herein, responded very efficiently to mass increase at the sensor surface due to precipitation of precipitating molecule.

Figure 3A:
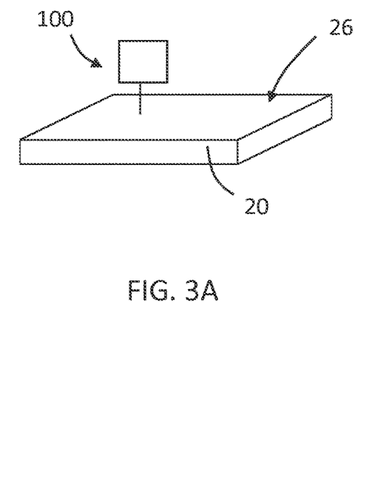
FIGS. 3A-B are schematic drawings illustrating an embodiment of analyte-coupled redox causing precipitation on a surface of a thin film resonator (TFR).
Figure 3B:
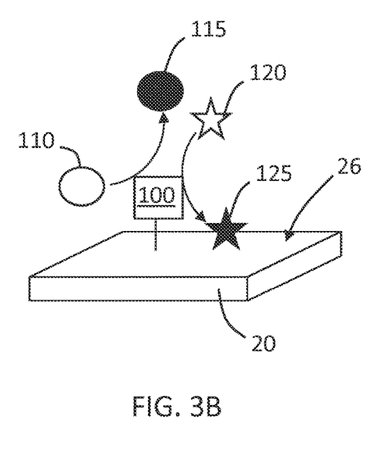

Referring now to FIGS. 3A-B, schematic drawings illustrating analyte-coupled redox of a soluble precipitation precursor to convert the precursor to a precipitating molecule and precipitation of the precipitating molecule on the surface of a TFBAR are shown. As depicted in FIG. 3A, an intermediate electron transfer agent 100 is immobilized on a surface 26 of a resonator 20. Preferably, the intermediate electron transfer agent 100 is configured to selectively interact with one or both of the analyte 110 or the soluble precipitation precursor 120 (see FIG. 3B). In some embodiments, the intermediate electron transfer agent 100 is configured to selectively interact with the soluble precipitation precursor 120 to oxidize or reduce the precursor in proximity to the surface 26 of the sensor 20. Accordingly, the resulting precipitating molecule 125 is produced in proximity to the surface 26 of the sensor 20. In the embodiment depicted in FIG. 3B, the intermediate electron transfer agent 100 oxidizes or reduces the analyte 110 to generate a redox analyte product 115 and reduces or oxidizes the soluble precipitation precursor 120 to generate the precipitating molecule 125, which can precipitate on the surface 26 of the sensor 20. The analyte 110 and the soluble precipitation precursor 120 can be added in solution, suspension or the like and moved across the resonator 20.

Figure 4:
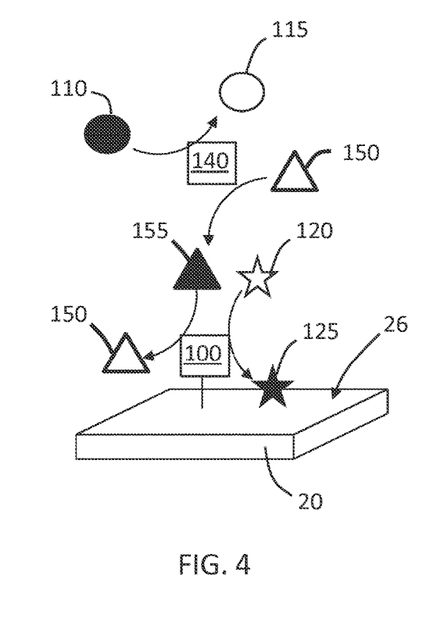
FIGS. 4-6 are schematic drawings illustrating some embodiments of analyte-coupled redox causing precipitation on a surface of a TFR.
Figure 5:
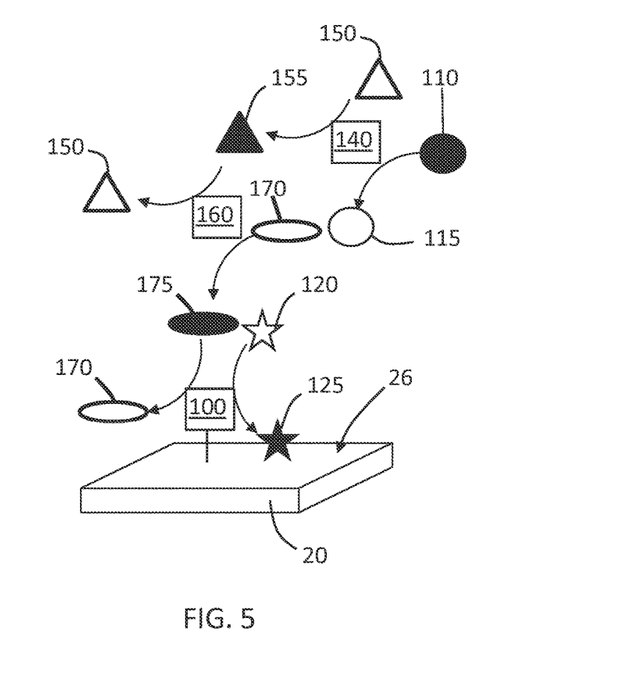

Any suitable number of intermediate electron transfer agents may be employed to effectively couple redox of the analyte with redox of the soluble precipitation molecule. Referring now to FIGS. 4-5, embodiments employing multiple intermediate electron transfer agents, and associated redox cofactors, are depicted.

In the embodiment depicted in FIG. 4, first 100 and second 140 intermediate electron transfer agents are employed. In the depicted embodiment, the second intermediate electron transfer element 140 oxidizes or reduces the analyte 110 to the redox analyte product 115. The second intermediate electron transfer element 140 also reduces or oxidizes a redox cofactor 150 to a cofactor redox product 155. The first intermediate electron transfer agent 100 oxidizes or reduces the cofactor redox product 155 to the redox cofactor 150 and reduces or oxidizes the soluble precipitation precursor 120 to generate the precipitating molecule 125, which can precipitate on the surface 26 of the resonator 20. In the depicted embodiment, the first intermediate electron transfer element 100 is bound to the surface 26 of the sensor 20. However, it will be understood that either one or both of the first 100 and second 140 intermediate electron transfer agents may be bound to the surface of the resonator. The cofactor 150, soluble precipitation substrate 120, analyte 110 and optionally one of the first 100 or second 140 electron transfer agents (if not bound to the surface of the resonator or if additional agent desired) may be introduced in solution across the resonator.

In the embodiment depicted in FIG. 5, first 100, second 140 and third 160 intermediate electron transfer agents are employed. In the depicted embodiment, the second intermediate electron transfer element 140 oxidizes or reduces the analyte 110 to the redox analyte product 115. The second intermediate electron transfer element 140 also reduces or oxidized a first redox cofactor 150 to a first cofactor redox product 155. The third intermediate electron transfer element 160 oxidizes or reduces the first cofactor redox product 155 to the first redox cofactor 150. The third intermediate electron transfer element 160 also reduces or oxidized a second redox cofactor 170 to a second cofactor redox product 175. The first and second redox cofactors may the same. The first intermediate electron transfer agent 100 oxidizes or reduces the second cofactor redox product 175 to the second redox cofactor 170 and reduces or oxidizes the soluble precipitation precursor 120 to generate the precipitating molecule 125, which can precipitate on the surface 26 of the resonator 20. In the depicted embodiment, the first intermediate electron transfer element 100 is bound to the surface 26 of the sensor 20. However, it will be understood that two or more of the first 100, second 140 and third 160 intermediate electron transfer elements may be bound to the surface of the resonator. The first 150 and second 170 cofactors (if different), soluble precipitation substrate 120, analyte 110 and optionally one of the first 100, second 140 or third 160 electron transfer agents (if not bound to the surface of the resonator or if additional agent desired) may be introduced in solution, suspension or the like across the resonator.

As indicated above, any suitable number of intermediate electron transfer agents and cofactors, if needed, can be used to couple redox of the analyte with redox of the soluble precipitation precursor. Any one or more of the intermediate electron transfer agents may be immobilized on the surface of the resonators. In some embodiments, no intermediate electron transfer agents are bound to the surface of the resonator. In some embodiments, one or more redox reagents, such as a cofactor, are immobilized to the surface of the resonator. In some embodiments, one or more intermediate electron transfer agents and one or more other redox reagents are immobilized on the surface of the resonator.

For biological analytes, the first intermediate electron transfer agent is preferably an analyte-selective enzyme having a high affinity for the analyte and capable of catalyzing oxidization or reduction of the analyte. Examples of such enzymes include dehydrogenases or reductases, heme metabolism enzymes, oxidative stress-related enzymes, oxygenases or hydroxylases and the like. Examples of dehydrogenases or reductases include hydroxysteroid dehydrogenases, alcohol dehydrogenase, aldehyde dehydrogenases, aldo-keto reductases, biliverdin reductases, 2,4-dienoyl CoA reductases, dihydrofolate reductases, glyceraldehyde phosphate dehydrogenases, Gamma-interferon-inducible lysosomal thiol reductase, glutamate dehydrogenases, glutathione reductases, ioscitrate dehydrogenases, lactate dehydrogenases, pyruvate dehydrogenases, cytochrome P450 reductases, quinoid dihydropteridine reductase, thioredoxin reductases, WW domain containing oxioreductase and the like. Examples of heme metabolism enzymes include biliverdin reductases, heme oxidases and the like. Examples of oxidative stress-related enzymes include aldehyde oxidase, catalase, cyclooxygenases, ERp57/PDIA, glutaredoxins, glutathione peroxidases, myeloperozidases, nitric oxide synthetases, peroxiredoxins, superoxide dismutases, thioredoxins, thioredoxin reductases and the like. Examples of oxygenases or hydroxylases include aldehyde oxidases, cyclooxygenases, dopamine beta-hydrozylae, prolyl hydroxylases, guanosine triphosphate (GTP) cyclohydrolases, hydroxacid oxidases, indoleamine dioxygenases, kynureine 3-monooxygenases, lipoxygenases, lysyl oxidases, monoamine oxidases, peptidylglycine alpha-amidating monooxygenases, protein disulfide isomerases, tryptophan hydroxylases, glucose oxidases and the like.

Some redox enzymes work more efficiently with or require redox cofactors. Accordingly, it can be desirable to include one or more suitable cofactor in a liquid mixture or solution containing the enzyme and any other intermediate electron transfer agent, the one or more soluble precipitation precursors, and the analyte (if present). Redox cofactors can be organic or inorganic redox cofactors. Examples of inorganic cofactors include cupric ions, ferric or ferrous ions, magnesium ions, manganese ions, molybdenum ions, nickel ions, zinc ions, iron-sulfur clusters and the like. Examples of organic cofactors include nicotine adenine dinucleotide (NAD+), flavin adenine dinucleotide (FAD), lipoamide, ascorbic acid, flavin mononucleotide (FMN), coenzyme F420, coenzyme B, coenzyme Q, glutathione, heme, pyrroloquinoline quinone, tetrahydrobiopterin, and the like.

In some embodiments, an intermediate electron transfer agent is an enzyme that is capable of converting a soluble precipitation precursor that is soluble in the assay environment to an insoluble precipitating molecule that precipitates on the surface of the resonator. Examples of enzyme/precipitation precursor systems that are capable of producing an insoluble precipitating molecule which is capable of accumulating on a surface of a TFBAR include peroxidase enzymes, for example horse radish peroxidase (HRP) or myeloperoxidase, and one of the following: benzidene, benzidene dihydrochloride, diaminobenzidene, o-tolidene, o-dianisidine and tetramethyl-benzidene, carbazoles, particularly 3-amino-9-ethylcarbazole, and various phenolic compounds all of which have been reported to form precipitates upon reaction with peroxidases. In some embodiments a peroxidase is coupled to a specific analyte oxidation by an oxidase where one of the end product is a peroxide (e.g., glucose oxidase oxidation of glucose), which is coupled with a soluble precipitation precursor that precipitates when oxidized. The reduced cofactors generated by the analyte specific oxidation by dehydrogenases may be coupled to reduction, and subsequent precipitation of, for example, tetrazoliums salts as insoluble formazans such as nitro-blue tetrazolium chloride (NBT), 2-(4-iodophenyl)-3-(4-nitrophenyl)-phenyl-2H-tetrazolioum chloride (INT) or 3-(4,5-dimethyl-2-thiazolyl)-2, 5-diphenyl-2H-tetrazolium bromide (MTT) via the enzyme diaphorase which functions as an intermediate electron transfer agent.

In some embodiments, an intermediate electron transfer agent can be a chemical such as phenazine methosulfate which facilitates the reduction and subsequent precipitation of, for example, formazans such as nitro-blue tetrazolium chloride (NBT), 2-(4-iodophenyl)-3-(4-nitrophenyl)-5-phenyl-2H-tetrazolium chloride (INT) or 3-(4,5-dimethyl-2-thiazolyl)-2, 5-diphenyl-2H-tetrazolium bromide (MTT) by reduced cofactors, such as NADH or NADPH, generated during the analyte specific oxidation by a dehydrogenase.

Figure 6:
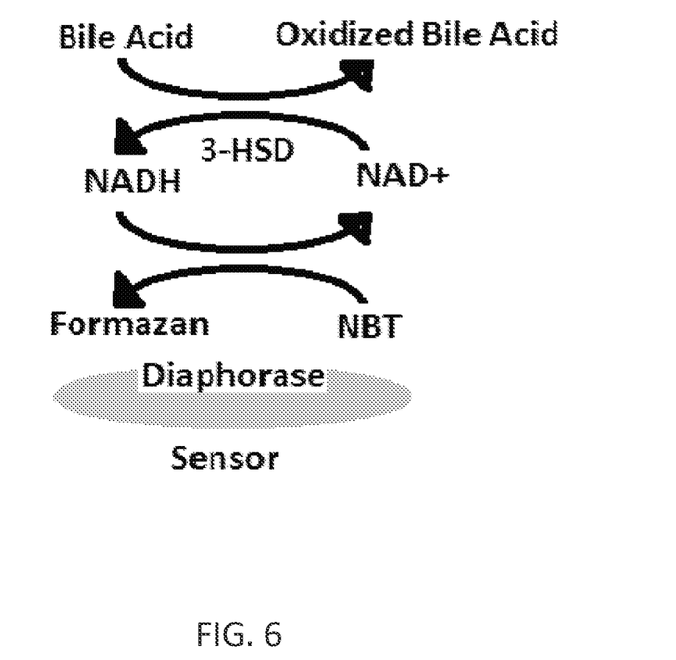

Referring now to FIG. 6, an embodiment of an analyte detection system is schematically depicted. In the depicted embodiment, diaphorase (an intermediate electron transfer agent) is immobilized on a surface of a sensor. The diaphorase enzyme catalyzes the reduction of tetrazolium (e.g., NBT) to insoluble formazan by a reduced cofactor such as NADH or NADPH. During specific oxidization of an analyte (bile acid in the depicted embodiment) by an enzyme (3-alpha-hydroxysteroid dehydrogenase or 3-HSD in the depicted embodiment) NADH or NADPH is generated as an electron carrier cofactor used by the enzyme. The amount of formazan that precipitates on the surface or the rate of formazan precipitation can be correlated to the amount of bile acid in the assay mixture.

It will be understood that FIG. 6 presents only one embodiment of a specific assay that may be employed for detecting the presence or amount of an analyte in a sample through analyte-coupled redox causing precipitation on a surface of a sensor, such as a TFBAR. For example, any suitable intermediate electron acceptor, such as an enzyme, (e.g., those described above) may be employed to convert a soluble precipitation precursor (NBT in the depicted embodiment) to an insoluble precipitating molecule (formazan in the depicted embodiment) may be employed. The enzyme need not be coupled to the surface of the receptor. By way of further example, any one or more additional intermediate electron acceptors, such as an analyte-selective enzyme (3-HSD in the depicted embodiment) may be employed. The intermediate electron transfer agent may be bound to the surface of the sensor or may be free in the assay mixture. Any suitable cofactors or analytes may be employed.

Examples of suitable analytes that may be employed (i.e., the presence or amount of which can be assayed using a system as described herein) include any analyte capable of undergoing a redox reaction. Preferably, the analyte is employed with an analyte-selective intermediate electron transfer agent that can catalyze or otherwise facilitate oxidization or reduction, as the case may be, of the analyte. In preferred embodiments, the analyte-selective intermediate electron transfer agent is an enzyme. Examples of redox analytes having analyte-selective redox enzymes include bile acids (enzyme can be 3-HSD or the like), glucose (enzyme can be glucose oxidase or glucose dehydrogenase), and the like. It will be understood that an "analyte" may be a class of compounds, such as bile acids; a specific compound, such as glucose; or both a class of compounds and a specific compound. In some embodiments, the analyte of interest may be any enzyme that is capable of performing an oxidation or reduction reaction.

In some embodiments, a polymer precipitates from solution onto a surface of the resonator. The polymer can be formed from monomers, which serve as the soluble precipitation precursor. Redox polymerization initiators may be used to initiate such polymerization and couple redox of the analyte to precipitation of the polymer. Examples of redox initiators include ammonium peroxydisulfate-sodium bisulfide, ceric ammonium nitrate, peroxides such as hydrogen peroxide, alkyl hydrogen peroxides, peroxydisulfates, peroxydiphosphates, and the like. In some embodiments, the polymerization initiator is immobilized to the surface of the resonator; e.g., through coupling via another molecule. In such embodiments, the forming polymer grafts from the surface. For the purposes of the present disclosure, a polymer grafted to the surface of the resonator is considered an insoluble precipitating molecule, even if the polymer would be soluble in the solvent or liquid medium if the polymer were not grafted to the surface of the resonator.

Figure 7A:
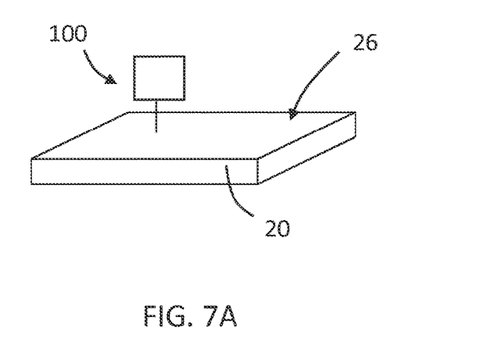
FIGS. 7A-C are schematic drawings illustrating an embodiment of analyte-coupled redox causing polymerization grafted from a surface of a TFR.
Figure 7B:
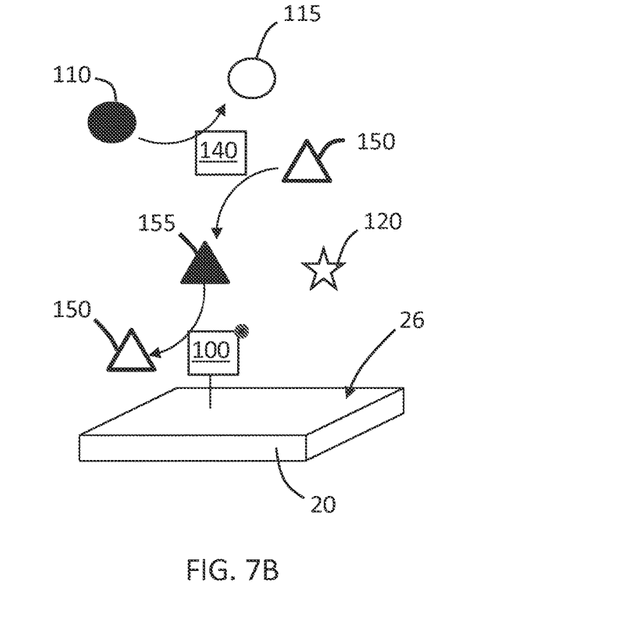
Figure 7C:
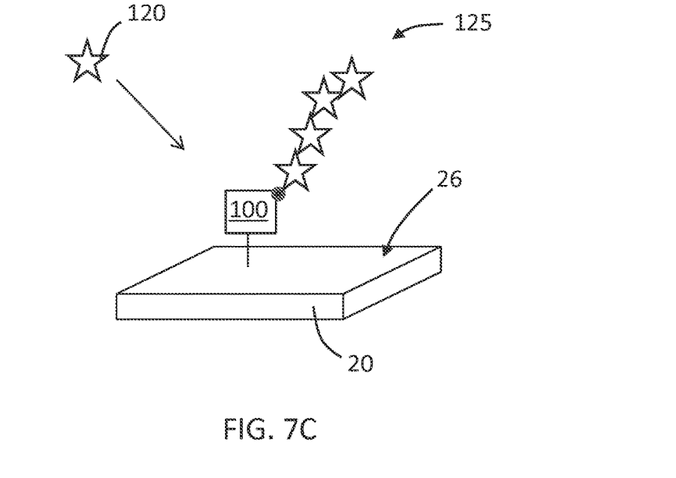

Referring now to FIGS. 7A-7C, schematic drawings illustrating an embodiment where a redox polymerization initiator 100 is grafted to the surface 26 of a resonator 20 is shown. The redox polymerization initiator 100 serves as an intermediate electron transfer agent in this embodiment. Prior to addition of reagents (FIG. 7A), the polymerization initiator is not activated and not configured to initiate polymerization. However, after reagents are added, the polymerization initiator 100 is activated, if the analyte 110 is present, and serves to initiate polymerization of monomers 120. The added reagents include analyte 100 or sample suspected of containing analyte, intermediate electron transfer agent 140, redox cofactor 150 and monomer 120. Preferably, intermediate electron transfer agent 140 selectively interacts with analyte 110 and facilitates oxidization or reduction of analyte 110 to analyte redox product 115. Intermediate electron transfer agent 140 also facilitates reduction or oxidization of cofactor 150 to cofactor redox product 155. Cofactor redox product 155 interacts with polymerization initiator (intermediate electron transfer agent) 100 to activate polymerization initiator and monomers 120 can polymerize from the grafted initiator 100 to form polymer (precipitating molecule) 125.

It will be understood that FIGS. 7A-C represent one embodiment of how the use of a redox polymerization initiator may be employed as an intermediate electron transfer agent to couple redox of an analyte with precipitation of a polymer on a surface of a sensor. For example, the polymerization initiator need not be immobilized to the surface of the sensor. By way of further example, both the intermediate electron transfer agent selective for the analyte and the polymerization initiator may be bound to the surface of the resonator. By way of yet another example, one or more additional intermediate electron transfer agents or cofactors may be employed.

Any suitable method for immobilizing an intermediate electron transfer agent on a surface of a TFBAR may be used. By way of example, a uniform coating of epoxy silane may be deposited on the sensor surface using a vapor deposition process. Test and reference intermediate electron transfer agents, such as a polymerization initiator (which may be conjugated to a molecule having appropriate functionality for coupling to the surface of the resonator), an enzyme or the like, may then be deposited onto test and reference resonators using, for example, piezo based nanodispensing technology. Primary amines on the intermediate electron transfer agents react with the epoxide groups covalently binding the electron transfer agent to the sensor surface. By way of further example, a thiol group, if present, of the electron transfer agent may bind to a sulfur or sulfhydryl group on the surface, or coated to the surface, of the TFBAR. The surface of the TFBAR may be modified, as appropriate or necessary, to permit binding of the intermediate electron transfer agent.

In various embodiments, the presence or activity of a redox enzyme can be detected using principles similar to those described above with regard to detection of an analyte. The analyte could be considered to be an enzyme and the amount, activity or the amount and activity of the enzyme may be detected generally as described above. It will be understood that greater activity with less amount of enzyme may result in a greater signal than less activity with more enzyme. Accordingly, in embodiments, the combination of activity and amount of a redox enzyme can be detected in a sample. A test sample putatively including a redox enzyme can be combined with a known amount of a substrate that can be oxidized or reduced by the enzyme. The oxidization or reduction of the substrate can be coupled to oxidization or reduction of a soluble precursor via a redox cascade that results in a precipitating molecule precipitating on a surface of the TFBAR. The change in mass on the surface of the TFBAR can be correlated with activity of the enzyme in the test sample.

One or more intermediate electron transfer elements or other redox reagents, such as cofactors, can be coupled to the surface of a TFBAR; e.g., as described above. In this case the enzyme to be detected will be added in the sample and will not serve as TFBAR bound intermediate electron transfer element.

By way of illustration and with reference to FIG. 4, the redox enzyme to be detected can be considered element 140. A known amount of substrate 110 for the enzyme can be mixed with the enzyme 140 before or as the sample containing the enzyme 140 is moved across the surface 26 of the sensor 20. If the enzyme 140 is present and has activity, the enzyme 140 can oxidize or reduce the substrate 110 to a redox substrate product 115. In the depicted embodiment, the enzyme 140 also reduces or oxidizes a redox cofactor 150 to a cofactor redox product 155. An intermediate electron transfer agent 100 oxidizes or reduces the cofactor redox product 155 to the redox cofactor 150 and reduces or oxidizes the soluble precipitation precursor 120 to generate the precipitating molecule 125, which can precipitate on the surface 26 of the resonator 20. The cofactor 150, soluble precipitation substrate 120, substrate 110 and enzyme 140 may be introduced in solution across the resonator to which the intermediate electron transfer element 100 is bound.

While described with regard to FIG. 4, it will be understood that detection of the presence or activity of an enzyme can be accomplished by suitable modification of any appropriate embodiments described above with regard to detection of an analyte. For example, the enzyme may be substituted for intermediate electron transfer element 140 or 160 in FIG. 6 and the substrate may be substituted for element 150 or 170.

Uses

The sensors, devices and systems described herein may be employed to detect an analyte in a sample. The sensors may find use in numerous chemical, environmental, food safety, or medial applications. By way of example, a sample to be tested may be, or may be derived from blood, serum, plasma, cerebrospinal fluid, saliva, urine, and the like. Other test compositions that are not fluid compositions may be dissolved or suspended in an appropriate solution or solvent for analysis.

Definitions

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances.

Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

As used herein, a "redox analyte" is an analyte capable of being oxidized or reduced. Preferably, the redox analyte is capable of interacting with a redox enzyme that can catalyze the oxidization or reduction of the analyte.

As used herein, an intermediate electron transfer agent or enzyme that is "selective" for a molecule is a transfer agent or enzyme that selectively interacts with the molecule, such as an analyte or a precipitation precursor. "Selectively interacts" means interacts with the molecule of interest with a substantially higher degree of specificity than with other molecules. For example, a selective transfer agent or enzyme can interact with a molecule of interest with a 5-fold or higher (e.g., 10-fold or higher, 50-fold or higher, or 100-fold or higher) specificity than with other reagents present in an assay mixture. In some cases, an electron transfer agent or an enzyme may be selective for more than one molecule (e.g., an analyte and a cofactor or a precipitation precursor and a cofactor).

EXAMPLES

The following non-limiting examples serve to describe more fully the manner of using the above described sensors, methods, devices and systems. It is understood that these examples in no way serve to limit the scope of this disclosure or claims that follow, but rather are presented for illustrative purposes.

Example 1

Analyte-Coupled Redox of Precipitating Molecule—Proof of Concept

Figure 8:
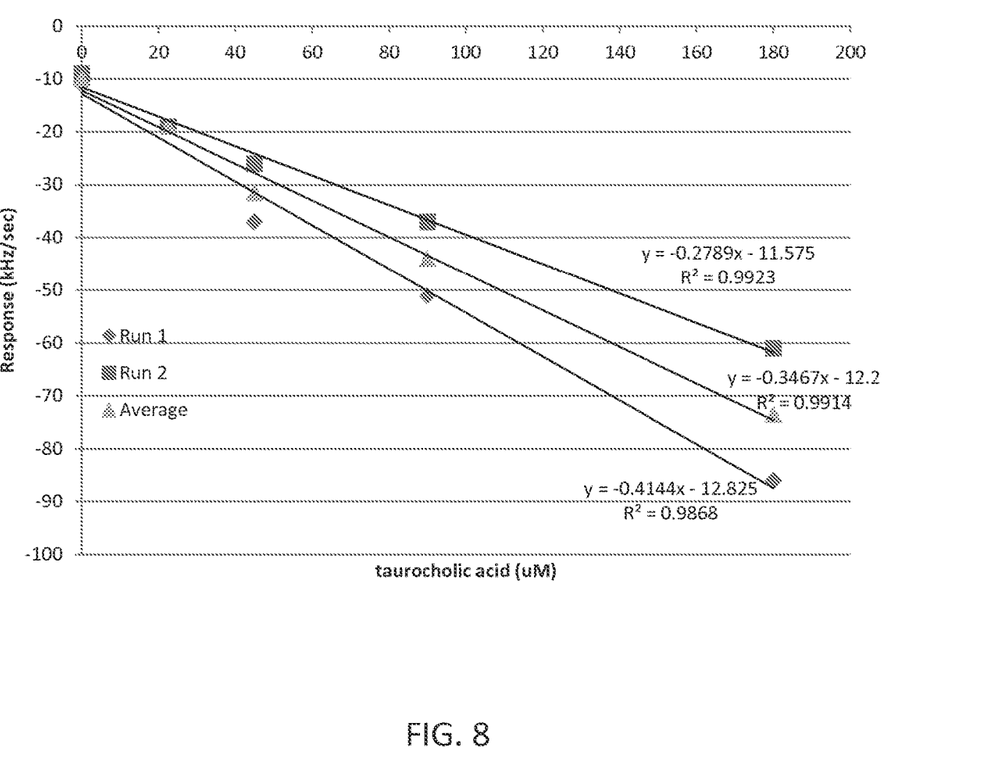
FIG. 8 is a plot showing change in frequency at a particular phase of a resonator employed an assay generally as depicted in FIG. 6.

The following example employed an assay system generally as depicted in FIG. 6. The results are presented in FIG. 8. FIG. 8 shows the dose response of taurocholic acid spiked into normal human serum in a clinically useful range. The reaction mixture included 1.75 mM NAD+, 0.4 mg/mL NBT, 0.1 U/mL 3-HSD in Tris pH 7.5. Sensors were epoxy silane coated Rev 3 sensors coated with 0.2 mg/mL diaphorase (test channel) and 0.2 mg/mL BSA (reference channel). The assay combined 60 uL Reaction Mixture, 10 uL sample, 38 uL Tris pH 7.5, which was passed over the sensor for 2 minutes. Data analyzed and shown in FIG. 8 is the linearly fit the first 15 seconds of response data.

Thus, embodiments of MASS DETECTION THROUGH REDOX COUPLING are disclosed. One skilled in the art will appreciate that the methods, devices and systems described herein can be practiced with embodiments other than those disclosed. The disclosed embodiments are presented for purposes of illustration and not limitation. One will also understand that components of the methods, devices and systems depicted and described with regard the figures and embodiments herein may be interchangeable.

What is claimed is:

1. A method for detecting an analyte in a sample, comprising:
    introducing a mixture comprising a redox analyte, one or more intermediate electron transfer agents, a soluble precipitation precursor, and, optionally or if needed, one or more redox cofactors, in proximity to a surface of a thin film bulk acoustic resonator (TFBAR),
    wherein the redox analyte in the presence of the one or more intermediate electron transfer agents, optional or required cofactors, and soluble precipitation precursor causes redox of the soluble precipitation precursor to generate a precipitating molecule that precipitates on the surface of the TFBAR; and
    measuring mass added at the surface of the TFBAR, wherein measuring the mass added at the surface of the TFBAR comprises actuating the TFBAR into an oscillating motion and measuring one or more resonator output signals representing resonance characteristics of the oscillating motion of the TFBAR.

2. The method of claim 1, wherein at least one or more of the intermediate electron transfer agents are immobilized on the surface of the TFBAR.

3. The method of claim 1, wherein at least one of the intermediate electron transfer agents is an enzyme selective for the analyte.

4. The method of claim 1, wherein at least one of the electron transfer agents is selective for the soluble precipitation precursor.

5. The method of claim 1, wherein the mixture comprises at least two intermediate electron transfer agents, wherein at least one of the intermediate electron transfer agents is an enzyme selective for the analyte and wherein at least one of the electron transfer agents is selective for the soluble precipitation precursor.

6. The method of claim 1, wherein measuring the mass added to the surface of the TFBAR comprises:
    coupling an input electrical signal to the TFBAR, the input electric signal having a frequency within a resonance band of the piezoelectric resonator, wherein the frequency is about 900 MHz or greater;
    transmitting the input electrical signal through or across the TFBAR to generate an output electrical signal having a frequency;
    receiving the output electrical signal from the TFBAR; and
    determining a change in phase shift of the output electrical signal caused by deposition of the precipitate on the surface of the TFBAR.

7. The method of claim 6, wherein the change in phase shift is a change in insertion or reflection coefficient phase shift.

8. The method of claim 1, wherein measuring the mass added to or bound to the surface of the TFBAR comprises:
    actuating the TFBAR into an oscillating motion at a frequency of about 900 MHz or greater;
    measuring one or more resonator output signals representing resonance characteristics of the oscillating motion of the TFBAR; and
    adjusting the actuation frequency of the sensing resonator to maintain a resonance point of the TFBAR.

9. The method of claim 8, wherein the resonance point of the TFBAR is a point of maximum group delay.

10. The method of claim 6, wherein the frequency is about 1.8 GHz or greater.

11. The method of claim 1, wherein at least one of the intermediate electron transfer elements is an enzyme.

12. A system for detecting an analyte in a sample, comprising:
a thin film bulk acoustic resonator (TFBAR) comprising a surface to which a first electron transfer agent is immobilized,
the first electron transfer agent being configured to selectively bind an analyte or a soluble precipitation precursor,
the TFBAR having a resonance frequency of 900 MHz or greater;
one or more containers housing the precipitation precursor and, optionally or if required, one or more redox cofactors;
a fluid path from the one or more containers to the surface of the TFBAR to which the first electron transfer agent is bound;
a fluid path for introduction of the analyte with the precipitation precursor;
actuation circuitry configured to drive the TFBAR in an oscillating motion;
measurement circuitry arranged to be coupled to the TFBAR and configured to measure one or more resonator output signals representing resonance characteristics of the oscillating motion of the sensing resonator; and
a controller operatively coupled with the actuation and measurement circuitry.

13. A method for detecting activity or presence of an enzyme in a sample, comprising:
introducing a mixture comprising one target redox enzyme, one or more redox substrates for the target redox enzyme, one or more intermediate electron transfer agents, a soluble precipitation precursor, and, optionally or if needed, one or more redox cofactors, in proximity to a surface of a thin film bulk acoustic resonator (TFBAR),
wherein the redox enzyme in the presence of the one or more redox substrates and one or more intermediate electron transfer agents, optional or required cofactors, and soluble precipitation precursor causes redox of the soluble precipitation precursor to generate a precipitating molecule that precipitates on the surface of the TFBAR; and
measuring mass added at the surface of the TFBAR, wherein measuring the mass added at the surface of the TFBAR comprises actuating the TFBAR into an oscillating motion and measuring one or more resonator output signals representing resonance characteristics of the oscillating motion of the TFBAR.

14. The method of claim 13, wherein at least one or more of the intermediate electron transfer agents are immobilized on the surface of the TFBAR.

15. The method of claim 13, wherein at least one of the electron transfer agents is selective for the soluble precipitation precursor.

16. The method of claim 13, wherein measuring the mass added to our bound to the surface of the TFBAR comprises:
coupling an input electrical signal to the TFBAR, the input electric signal having a frequency within a resonance band of the piezoelectric resonator, wherein the frequency is about 900 MHz or greater;
transmitting the input electrical signal through or across the TFBAR to generate an output electrical signal having a frequency;
receiving the output electrical signal from the TFBAR; and
determining a change in phase shift of the output electrical signal caused by deposition of the precipitate on the surface of the TFBAR.

17. The method of claim 16, wherein the change in phase shift is a change in insertion or reflection coefficient phase shift.

18. The method of claim 13, wherein measuring the mass added to or bound to the surface of the TFBAR comprises:
actuating the TFBAR into an oscillating motion at a frequency of about 900 MHz or greater;
measuring one or more resonator output signals representing resonance characteristics of the oscillating motion of the TFBAR; and
adjusting the actuation frequency of the sensing resonator to maintain a resonance point of the TFBAR.

19. The method of claim 18, wherein the resonance point of the TFBAR is a point of maximum group delay.

20. A system for detecting activity or presence of a redox enzyme in a sample, comprising:
a thin film bulk acoustic resonator (TFBAR) comprising a surface to which a first electron transfer agent is immobilized,
the first electron transfer agent being configured to selectively bind an analyte or a soluble precipitation precursor,
the TFBAR having a resonance frequency of 900 MHz or greater;
one or more containers housing a substrate for the redox enzyme, the precipitation precursor and, optionally or if required, one or more redox cofactors;
a fluid path from the one or more containers to the surface of the TFBAR to which the first electron transfer agent is bound;
a fluid path for introduction of the enzyme with the substrate, the precipitation precursor and, optionally or if required, one or more redox cofactors;
actuation circuitry configured to drive the TFBAR in an oscillating motion;
measurement circuitry arranged to be coupled to the TFBAR and configured to measure one or more resonator output signals representing resonance characteristics of the oscillating motion of the sensing resonator; and
a controller operatively coupled with the actuation and measurement circuitry.

* * * * *

UNITED STATES PATENT AND TRADEMARK OFFICE
CERTIFICATE OF CORRECTION

PATENT NO. : 10,488,407 B2
APPLICATION NO. : 15/511130
DATED : November 26, 2019
INVENTOR(S) : Michael Salvati and Ian Robert Harmon Page 1 of 1

It is certified that error appears in the above-identified patent and that said Letters Patent is hereby corrected as shown below:

In the Claims

Column 16, Line 2, Claim 16 replace "our" with --or--

Signed and Sealed this
Twenty-fourth Day of March, 2020

Andrei Iancu
*Director of the United States Patent and Trademark Office*